United States Patent [19]

Chang et al.

[11] 4,013,732

[45] Mar. 22, 1977

[54] CONVERSION OF METHANOL TO GASOLINE WITH MINIMUM DURENE PRODUCTION

[75] Inventors: Clarence D. Chang, Princeton; William H. Lang, Pennington, both of N.J.

[73] Assignee: Mobil Oil Corporation, New York, N.Y.

[22] Filed: Oct. 17, 1975

[21] Appl. No.: 623,239

[52] U.S. Cl. .................. 260/668 R; 260/DIG. 33
[51] Int. Cl.² .......................................... C07C 1/20
[58] Field of Search ............... 260/668 R, DIG. 33

[56] References Cited

UNITED STATES PATENTS

| 3,894,103 | 7/1975 | Chang et al. | 260/668 R |
| 3,894,104 | 7/1975 | Chang et al. | 260/668 R |
| 3,894,105 | 7/1975 | Chang et al. | 260/668 R |

*Primary Examiner*—Veronica O'Keefe
*Attorney, Agent, or Firm*—Charles A. Huggett; Carl D. Farnsworth

[57] ABSTRACT

The conversion of methanol to gasoline boiling hydrocarbons of low durene content is accomplished with a ZSM5 crystalline zeolite alone or supported by a binder-matrix material comprising primarily materials other than alumina.

6 Claims, No Drawings

4,013,732

CONVERSION OF METHANOL TO GASOLINE WITH MINIMUM DURENE PRODUCTION

BACKGROUND OF THE INVENTION

It has recently been discovered, and is elsewhere patented, that lower organic compounds containing hetero-atoms, such as oxygen, sulfur and/or halogen, are convertible over a special class of crystalline zeolite catalysts at elevated temperatures to form hydrocarbons in the gasoline boiling range. This conversion is carried out at a temperature in the range of about 500 to 1200° F, preferably at temperature in the range of about 600 to 850° F at space velocities in the range of about 0.5 to 50 LHSV. The product obtained comprises water, light hydrocarbon gases ($C_4^-$) and a normally liquid hydrocarbon fraction ($C_5^+$) which contains a substantial amount, usually at least about half, of $C_6$ to $C_{10}$ monocyclic aromatic hydrocarbons.

It is also known and elsewhere disclosed that with a one carbon feed such as methanol, a portion of the produced aromatic hydrocarbons is durene (1,2,4,5 tetramethyl benzene). Durene is an undesirable component of gasoline because of its high melting point (174.7° F) and its tendency to crystallize out of solution at temperatures below 175° F. It has previously been recognized that one can increase the production of durene by carrying out the above described conversion at superatmospheric pressures. As an engineering matter, it is sometimes desirable to operate an industrial process of this type at elevated pressure. In this particular methanol operation, there are also some process advantages to be gained by operating at superatmospheric pressure. However, with the pressure responsive production of durene, substantial process operating compromises need to be made in order to produce a quality gasoline with an acceptably low durene content.

SUMMARY OF THE INVENTION

This invention resides in the discovery that catalyzing the conversion of lower alcohols, ethers and olefin components thereof and/or mixture thereof with a special class of crystalline zeolite conversion catalyst represented by ZSM5 crystalline zeolite to form gasoline boiling components of low durene content can be particularly pursued when employing a selected class of crystalline zeolite catalyst composition alone or in combination with a binder matrix substantially if not completely free of alumina as a binder component. Thus, substantially any inorganic oxide binder material of little or no alumina content may be employed to advantage as a support matrix material for the crystalline zeolite catalyst. On the other hand, it has also been found that metal aluminates and spinel type materials may be employed as a binder of matrix support component for the special crystalline zeolite catalyst in producing hydrocarbons with a low formation of durene. The influence of pressure on durene formation may be offset to some considerable extent by employing the particular crystalline zeolite catalyst compositions herein defined.

The conversion of methanol, dimethyl ether, and mixtures thereof to produce gasoline boiling hydrocarbons is carried out at a temperature within the range of 500° to 1000° F at a space velocity within the range of 0.5 to 50 LHSV. The pressure of the operation is preferably kept as low as possible for an efficient operation. Thus, the pressure may be as low as about atmospheric pressure or up to several hundred pounds of pressure. It is preferred that the pressure be not more than 750 psig and more usually less than about 600 psig. One particular feature of this invention is the discovery that the production of durene is reduced and suppressed even at the higher operating pressures when using a catalyst composition comprising a binder or matrix support of little or no alumina content. Thus, the novel catalyst composition of this invention comprises a special class of crystalline zeolite represented by ZSM5 crystalline zeolite admixed with a particular matrix material selected from the group consisting of a Group IVB metal oxide alone or combined with a Group IIB metal, or a mixture of IVB oxides as a binder material (support matrix) which is used in place of a binder or matrix comprising alumina such as gamma alumina. In one embodiment, the matrix material particularly comprises a mixture of $TiO_2$—$ZrO_2$. A $TiO_2$—$ZrO_2$ mixture has been reported in the literature as a relatively high surface area material with acidic properties. [Shibata and Kiyoura, Jr., Res., Inst., Cat., Hokkaido University 19, 35 (1971)]. In yet other embodiments, the binder or matrix material may be silicon oxide, titanium oxide, zinc titanium oxide, magnesium oxides and metal aluminates or spinels such as zinc aluminate. Thus, it has been found as shown in the examples discussed below that an alumina free matrix material used with the special crystalline zeolite herein identified improved aromatic selectivity by reducing the formation of durene and higher pressure may also be employed without undesirably increasing the formation of durene. Thus, it has been found the pressure restraints can be relaxed and more elevated pressures employed for reasons of economy to accomplish the conversions herein defined.

The binder or matrix support is preferably a material other than alumina or one containing only a very small amount of alumina. The term alumina refers to an alumina oxide and various oxide phases thereof. The term alumina does not refer to or include metal aluminate, spinels or aluminosilicates. The binder may contain a small amount of alumina, it being preferred that it be substantially free of aluminum oxide in order to minimize the formation of durene.

The lower alcohols that may be converted by the special zeolite catalyst composition of this invention include methanol, ethanol, n-propanol, and iso-propanol. The feed may consist of a relatively pure single alcohol, or mixtures of one or more of these alcohols with one another; or mixtures of one or more of these alcohols with an ether and an olefin components thereof. In general, any mixture comprising methanol and/or dimethyl ether, is a suitable feed for the formation of gasoline boiling components within the catalyst restrictions of this invention.

The special zeolite catalysts referred to herein utilize members of a special class of zeolites exhibiting some unusual properties. These zeolites induce profound transformations of aliphatic hydrocarbons to aromatic hydrocarbons in commercially desirable yields and are generally highly effective in alkylation, isomerization, disproportionation and other reactions involving aromatic hydrocarbons. Although they have unusually low alumina contents, i.e. high silica to alumina ratios, they are very active even with silica to alumina ratios exceeding 30. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at higher than usual temperatures to restore activity. In many environments, the zeolites of this class exhibit very low coke forming capability, conducive to very long times on stream between burning regenerations.

An important characteristic of the crystal structure of this class of zeolites is that it provides constrained access to, and egress from, the intra-crystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful as catalysts in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire and intracrystalline sorption capacity for normal hexane which is greater than that for water, i.e. they exhibit "hydrophobic" properties. It is believed that this hydrophobic character is advantageous in the present invention.

The zeolites useful as catalysts in this invention freely sorb normal hexane and have a pore dimension greater than about 5 Angstroms. In addition, their structure must provide constrained access to some larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective. Zeolites with windows of twelve-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F for at least 15 minutes. The zeolite is then flushed with helium and the temperature adjusted between 550° F and 950° F to give an overall conversion between 10% and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Catalysts suitable for the present invention are those which employ a zeolite having a constraint index from 1.0 to 12.0. Constraint Index (CI) values for some typical zeolites including some not within the scope of this invention are:

| CAS | C.I. |
|---|---|
| ZSM-5 | 8.3 |
| ZSM-11 | 8.7 |
| ZSM-35 | 4.5 |
| TMA Offretite | 3.7 |
| ZSM-12 | 2 |
| ZSM-38 | 2 |
| Beta | 0.6 |
| ZSM-4 | 0.5 |
| Acid Mordenite | 0.5 |
| REY | 0.4 |
| Amorphous Silica-alumina | 0.6 |
| Erionite | 38 |

The above-described Constraint Index is an important and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above defined range of 1 to 12.

Thus, it should be understood that the "Constraint Index" value as used herein is an inclusive rather than an exclusive value. That is, a zeolite when tested by any combination of conditions within the testing definition set forth herein above to have a constraint index of 1 to 12 is intended to be included in the instant catalyst definition regardless that the same identical zeolite tested under other defined conditions may give a constraint index value outside of 1 to 12.

The class of zeolites defined herein is exemplified by ZSM-5, ZSM-11, ZSM-12, ZSM-21, ZSM-35, ZSM-38 and other similar material. Recently issued U.S. Pat.

No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

U.S. application Ser. No. 528,061, filed Nov. 29, 1974, the entire contents of which are incorporated herein by reference, describes a zeolite composition including a method of making it. This composition is designated ZSM-35 and is useful in this invention.

U.S. application Ser. No. 528,060, filed Nov. 29, 1974, the entire contents of which are incorporated herein by reference, describes a zeolite composition including a method of making it. This composition is designated ZSM-38 and is useful in this invention.

The x-ray diffraction pattern of ZSM-21 appears to be generic to that of ZSM-35 and ZSM-38. Either or all of these zeolites is considered to be within the scope of this invention.

The specific zeolites described, when prepared in the presence of organic cations, are substantially catalytically inactive, possibly because the intracrystalline free space is occupied by organic cations from the forming solution. They may be activated by heating in an inert atmosphere at 1000° F for one hour, for example, followed by base exchange with ammonium salts followed by calcination at 1000° F in air. The presence of organic cations in the forming solution may not be absolutely essential to the formation of this special type zeolite; however, the presence of these cations does appear to favor the formation of this special type of zeolite. More generally, it is desirable to activate this type zeolite by base exchange with ammonium salts followed by calcination in air at about 100° F for from about 15 minutes to about 24 hours.

Natural zeolites may sometimes be converted to this type zeolite by various activation procedures and other treatments such as base exchange, steaming, alumina extraction and calcination, alone or in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12 and ZSM-21, with ZSM-5 particularly preferred.

The zeolites used as catalysts in this invention may be in the hydrogen form or they may be base exchanged or impregnated to contain ammonium or a metal cation complement. It is desirable to calcine the zeolite after base exchange. The metal cations that may be present include any of the cations of the metals of Groups I through VIII of the periodic table. However, in the case of Group IA metals, the cation content should in no case be so large as to substantially eliminate the activity of the zeolite for the catalysis being employed in the instant invention. For example, a completely sodium exchanged H-ZSM-5 appears to be largely inactive for shape selective conversions required in the present invention.

In a preferred aspect of this invention, the zeolites useful as catalysts herein are selected as those having a crystal framework density, in the dry hydrogen form, of not substantially below about 1.6 grams per cubic centimeter. It has been found that zeolites which satisfy all three of these criteria are most desired. Therefore, the preferred catalysts of this invention are those comprising zeolites having a constraint index as defined above of about 1 to 12, a silica to alumina ratio of at least about 12 and a dried crystal density of not substantially less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference on Molecular Sieves, London, April, 1967" published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, seems to be important as the locus of catalytic activity.

Crystal framework densities of some typical zeolites including some which are not within the purview of this invention are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

DISCUSSION OF SPECIFIC EMBODIMENTS

The data presented below provides a comparison of results obtained with different catalyst compositions, in particular a comparison of binder or matrix support material used for effecting the conversion of methanol to gasoline boiling hydrocarbons. It will be observed from these data that the formation of durene was much less when using zeolite catalyst alone or in combination with binder support materials with and without the presence of alumina for pressures in the range of 0 to 750 psig.

Table 1 below presents a comparison of results obtained for methanol conversion as different pressures and a reactant space velocity of about 1.2.

TABLE 1

EFFECT OF BINDER ON DURENE FORMATION IN METHANOL CONVERSION OVER HZSM-5
700° F
1.2 WHSV*

| Binder (35 %) | NONE | | γ-Al$_2$O$_3$ | | | TiO$_2$ | | TiO$_2$-ZrO$_2$ | | | ZnTiO$_3$ | |
|---|---|---|---|---|---|---|---|---|---|---|---|---|
| Pressure, psig | 0 | 750 | 0 | 175 | 750 | 0 | 750 | 0 | 175 | 750 | 0 | 750 |
| Conversion, % | 100 | 100 | 100 | 100 | 100 | 100 | 100 | 100 | 100 | 100 | 100 | 100 |
| Hydrocarbons, wt % | | | | | | | | | | | | |
| C$_1$ | 43.3 | 40.2 | 44.8 | 37.2 | 31.6 | 40.6 | 47.4 | 46.1 | 42.9 | 46.2 | 44.5 | 42.5 |
| C$_5$+ | 56.7 | 59.8 | 55.2 | 62.8 | 68.4 | 59.4 | 52.6 | 53.9 | 57.1 | 53.8 | 55.5 | 57.5 |
| Durene in HC, wt % | 0.4 | 11.6 | 0.8 | 3.0 | 19.2 | 0.5 | 10.8 | 0.3 | 1.7 | 10.8 | 0.4 | 10.4 |

*Based on ZSM-5 component.

The reaction products of methanol conversion over the special zeolite catalyst will contain aliphatic and aromatic gasoline boiling range hydrocarbons along with some lower and higher boiling components. Water is also a product of the reaction. The products may contain some unreacted aliphatic intermediate materials and may be separated from desired gasoline boiling range material by any suitable method available in the art.

The results obtained with some other binder materials free of alumina under different space velocity conditions are shown in Table 2 below.

TABLE 2

EFFECT OF BINDER ON DURENE FORMATION IN METHANOL CONVERSION OVER HZSM-5
700°

| Binder | NONE | | SiO$_2$ | | MgO | ZnAl$_2$O$_4$ |
|---|---|---|---|---|---|---|
| Pressure, psig | 0 | 0 | 0 | 0 | 750 | 0 |
| WHSV, hr$^{-1}$ | 1.2 | 3.0 | 1.3 | 2.5 | 2.5 | 2.5 |
| Conversion, % | 100 | 100 | 100 | 100 | 99 | 100 |
| Hydrocarbons, wt % | | | | | | |
| C$_1$ | 43.3 | 42.7 | 30.6 | 40.8 | 47.1 | 46.8 |
| C$_5$+ | 56.7 | 57.3 | 69.4 | 59.2 | 52.9 | 53.2 |
| Durene in HC, wt % | 0.4 | 0.8 | 0.6 | 0.5 | 15.3 | 0.4 |

*WHSV based on HZSM-5 component.

It will be observed from the data of Table 2, that the binders or support materials examined were all low durene producers and produced less durene than the gamma alumina of Table 1. It is to be observed, however, that a metal aluminate such as zinc aluminate also was a low durene producer. It is, thus, concluded from these data that the presence of alumina as aluminum oxide alone in the catalyst composition operates to promote the formation of durene.

Having thus generally described the invention and discussed specific examples in support thereof, it is to be understood that no undue restrictions are to be imposed by reason thereof except as defined by the following claims.

We claim:

1. A method for converting a feed material selected from the group comprising methanol, dimethylether, and mixtures thereof to aliphatic and aromatic gasoline boiling components which comprises, passing the feed material at a temperature selected from within the range of 500° F to 1000° F and a pressure below 750 psig in contact with a special class of crystalline zeolite conversion catalysts represented by ZSM5 wherein the crystalline zeolite is used with a binder support material substantially free of aluminum oxide and, recovering an aromatic gasoline product of desired low durene concentration further controlled by using a low operating pressure.

2. The method of claim 1 wherein the crystalline zeolite is supported by a binder or matrix material selected from the group consisting of a Group IVB metal oxide alone a Group IVB metal oxide combined with one of a Group IIB metal or a mixture of Group IVB metal oxides.

3. The method of claim 1 wherein the matrix material comprises a mixture of titanium and zirconium oxides.

4. The method of claim 1 wherein the feed material comprises a mixture of lower alcohols.

5. The method of claim 1 wherein the catalyst comprises a mixture of ZSM5 crystalline zeolite and a titanium-zirconium oxide matrix material.

6. The method of claim 1 wherein the catalyst comprises a mixture of ZSM5 crystalline zeolite and a zinc-titanium oxide matrix material.

* * * * *